US005730955A

United States Patent [19]

Lohrmann

[11] Patent Number: 5,730,955
[45] Date of Patent: Mar. 24, 1998

[54] PROCESS FOR MAKING GAS-FILLED MICROSPHERES CONTAINING A LIQUID HYDROPHOBIC BARRIER

[75] Inventor: Rolf Lohrmann, La Jolla, Calif.

[73] Assignee: Molecular Biosystems, Inc., San Diego, Calif.

[21] Appl. No.: 477,510

[22] Filed: Jun. 7, 1995

Related U.S. Application Data

[63] Continuation-in-part of Ser. No. 284,782, Aug. 2, 1994, Pat. No. 5,562,893.
[51] Int. Cl.$^6$ .................................................. A61B 5/055
[52] U.S. Cl. .................................... 424/9.52; 128/662.02
[58] Field of Search .............................. 424/9.52, 9.51, 424/9.5, 489; 128/662.02

[56] References Cited

U.S. PATENT DOCUMENTS

| | | |
|---|---|---|
| 4,957,656 | 9/1990 | Cerny et al. . |
| 5,137,928 | 8/1992 | Erbel et al. . |
| 5,149,543 | 9/1992 | Cohen et al. . |
| 5,190,982 | 3/1993 | Erbel et al. . |
| 5,380,519 | 1/1995 | Schneider et al. .............. 424/9.52 |
| 5,409,688 | 4/1995 | Quay . |
| 5,413,774 | 5/1995 | Schneider et al. . |
| 5,508,021 | 4/1996 | Grinstaff et al. ............. 424/9.322 |
| 5,540,909 | 7/1996 | Schutt .......................... 424/9.52 |

FOREIGN PATENT DOCUMENTS

| | | |
|---|---|---|
| 0 458 745 | 11/1991 | European Pat. Off. . |
| 0 554 213 | 8/1993 | European Pat. Off. . |
| 0633030 | 1/1995 | European Pat. Off. . |
| WO 89/06978 | 8/1989 | WIPO . |
| WO 91/09629 | 7/1991 | WIPO . |
| WO 91/12823 | 9/1991 | WIPO . |
| WO 92/05806 | 4/1992 | WIPO . |
| WO 92/17213 | 10/1992 | WIPO . |
| WO 92/18164 | 10/1992 | WIPO . |
| WO 92/27212 | 10/1992 | WIPO . |
| WO 93/02712 | 2/1993 | WIPO . |
| WO 93/05819 | 4/1993 | WIPO . |
| WO 94/16739 | 8/1994 | WIPO . |
| WO 96/04018 | 2/1996 | WIPO . |

OTHER PUBLICATIONS

Ophir et al., "Contrast Agents in Diagnostic Ultrasound." *Ultrasound in Med. & Biol.* 15(4):319–333 (1989).

Schneider et al., "Polymeric Microballoons as Ulatrasound Contrast Agents–Physical and Ultrasonic Properties Compared with Sonicated Albumin." *Inv. Radiology* 27:134–139 (1992).

Wen et al., "Thermodynamics of Some Perfluorocarbon Gases in Water." *J. Solution Chem.* 8(3):225–246 (1979).

*Primary Examiner*—Gary E. Hollinden
*Assistant Examiner*—Michael G. Hartley
*Attorney, Agent, or Firm*—Morrison & Foerster

[57] ABSTRACT

A process for making gas-filled, pressure-resistant microspheres containing a liquid or solid hydrophobic barrier within the microsphere shell.

15 Claims, No Drawings

PROCESS FOR MAKING GAS-FILLED MICROSPHERES CONTAINING A LIQUID HYDROPHOBIC BARRIER

CROSS REFERENCE TO RELATED APPLICATIONS

This application is a continuation-in-part of application U.S. Ser. No. 08/284,782 filed Aug. 2, 1994, U.S. Pat. No. 5,562,893.

TECHNICAL FIELD

This invention is in the field of ultrasonic imaging. More particularly it relates to a process for increasing the hydrophobicity of microspheres useful for ultrasonic imaging. The microspheres comprising microbubbles of gas encapsulated by shells composed of a biocompatible, amphiphilic material contain a liquid or solid hydrophobic barrier formed on the inner surface of the microsphere shell. This barrier serves to decrease the rate of gas exchange between the microsphere and the aqueous environment surrounding the microsphere and thus enhances resistance to pressure instability due to gas exchange.

BACKGROUND

Diagnostic ultrasonic imaging is based on the principle that waves of sound energy can be focused upon an area of interest and reflected in such a way as to produce an image thereof. The ultrasonic transducer is placed on a body surface overlying the area to be imaged, and ultrasonic energy in the form of sound waves is directed toward that area. As ultrasonic energy travels through the body, the velocity of the energy and acoustic properties of the body tissue and substances encountered by the energy determine the degree of absorption, scattering, transmission and reflection of the ultrasonic energy. The transducer then detects the amount and characteristics of the reflected ultrasonic energy and translates the data into images.

As ultrasound waves move through one substance to another there is some degree of reflection at the interface. The degree of reflection is related to the acoustic properties of the substances defining the interface. If these acoustic properties differ, such as with liquid-solid, liquid-liquid or liquid-gas interfaces, the degree of reflection is enhanced. For this reason, gas-containing contrast agents are particularly efficient at reflecting ultrasound waves. Thus, such contrast agents intensify the degree of reflectivity of substances encountered and enhance the definition of ultrasonic images.

Ophir and Parker describe two types of gas-containing imaging agents: (1) free gas bubbles; and (2) encapsulated gas bubbles (*Ultrasound in Medicine and Biology* 15(4):319–x(1989)), the latter having been developed in an attempt to overcome instability and toxicity problems encountered using the former. Encapsulated gas bubbles, hereinafter referred to as "microspheres," are composed of a microbubble of gas surrounded by a shell of protein or other biocompatible material. One such imaging agent is ALBUNEX® (Molecular Biosystems, Inc., San Diego, Calif.) which consists of a suspension of air-filled albumin microspheres.

Generally, microspheres of a particular gas exhibit improved in vivo stability when compared to free bubbles of the same gas. However, most microspheres still have relatively short in vivo half lives which compromise their usefulness as contrast agents. This instability in vivo was thought to result from the collapse or breakdown of the shells under pressure resulting in rapid diffusion of the gas from the microspheres. Thus, many recent efforts have centered on improvements to the shell as a way of increasing in vivo stability. Known improvements relating to protein-shelled microspheres include coating the protein shell with surfactants (Giddy, PCT/WO 92/05806) and chemical cross-linking of the protein shell (Holmes et al., PCT/WO92/17213).

Additional efforts directed toward improving microsphere stability include the use of non-proteinaceous shell-forming materials. Bichon et al. (EPA 92/810367) and Schneider et al. (Inv. Radiol. 27:134–139 (1992)) describe the production of polymeric "microballoons" made of interfacially deposited polymers encapsulating various gases such as carbon dioxide, nitrous oxide, methane, freon, helium and other rare gases. Klaveness (PCT/WO92/17212) describes the use of chemically-linked, non-proteinaceous amphiphilic moieties encapsulating "air, nitrogen, oxygen, hydrogen, nitrous oxide, carbon dioxide, helium, argon, sulfur hexafluoride and low molecular weight, optionally fluorinated, hydrocarbons such as methane, acetylene or carbon tetrafluoride." Erbel et al. (U.S. Pat. No. 5,190,982) describe the use of polyamino-dicarboxylic acid-co-imide derivatives.

More recently, Schneider et al. (European Patent Application 554,213 A1) have demonstrated that microspheres containing gases with certain physical properties have improved stability. It is theorized that microsphere instability is caused by the increase in pressure to which microspheres are exposed once they are introduced into the circulatory system. Although Schneider et al. do not speculate as to the mechanism responsible for their observation of enhanced pressure resistance, we believe it is due to the effects of gas solubility on the rate of gas exchange with the aqueous environment.

According to Henry's law, the solubility of a given gas in solution increases as pressure increases. When a bubble of gas in solution is subjected to pressure, the rate of gas exchange between the gas in the bubble and the surrounding solution will increase in proportion to the amount of pressure, and the bubble of gas will eventually become completely solubilized. The more insoluble the gas is in the surrounding solution, the longer it will take for a bubble to become completely solubilized.

If the bubble of gas is surrounded by a shell, i.e., in the form of a microsphere, the effects of gas exchange are still observed, since microsphere shells do not completely eliminate contact between gas in the microsphere and the surrounding solution. Hence, when microspheres suspended in solution are subjected to pressure, the gas inside the microspheres eventually becomes solubilized in the surrounding solution which results in collapse of the microspheres.

Microspheres useful for ultrasonic imaging typically have shells with a certain degree of elasticity. This property is necessary for two important reasons. Firstly, microspheres with rigid shells may resonate at frequencies higher than those used for ultrasonic imaging and, thus, prove less efficient as contrast enhancers. On the other hand, a more rigid shell would tend to produce a lower attenuation. Secondly, rigid-shelled microspheres can crack or break when subjected to pressure and release the gaseous contents into the aqueous environment. Elastic-shelled microspheres, while able to overcome the aforementioned problems may unfortunately be more susceptible to the effects of gas exchange with the aqueous environment because of their tendency to be more permeable. This results in a greater degree of contact between the gas inside the microsphere and the surrounding aqueous environment thus facilitating gas exchange.

In order to inhibit the exchange of gas in the microsphere center with the surrounding aqueous environment, the present invention describes a process for increasing the hydrophobicity of the microsphere shell by forming a liquid hydrophobic barrier on the inner surface of the microsphere shell. Microspheres formed by this process will exhibit decreased water permeability and thus enhanced resistance to pressure instability due to gas exchange.

DISCLOSURE OF THE INVENTION

The present invention provides gas-filled microspheres containing a liquid or solid hydrophobic barrier on the inner surface of the microsphere shell which increases the overall hydrophobicity of the microsphere. In particular, the present invention provides for a process of producing microspheres comprising a shell formed from amphiphilic, biocompatible material surrounding a microbubble of at least one biocompatible gas and a liquid or solid hydrophobic compound barrier formed at the inner surface of the microsphere shell, said barrier decreasing the permeability of the shell and the rate of gas exchange with the aqueous environment surrounding the microsphere. In the present invention, a biocompatible gas suitable for use with the present invention is saturated with a hydrophobic "sealer" compound with a boiling point above room temperature. Upon cooling to room temperature, the hydrophobic compound will condense on the hydrophobic inner shell surface of the microsphere thereby creating an additional hydrophobic barrier and increasing the overall hydrophobicity of the microsphere shell. The hydrophobic compound can be inert and includes, but is not limited to, members of the hydrocarbon, halogenated hydrocarbon or perfluorocarbon series. The hydrophobic compound can have a linear, branched or cyclic molecular structure.

Hydrophobic compounds within the present invention, when introduced by a water-insoluble gas, can be reactive and capable of covalently bonding to reactive amino acid side chains in the protein of the shell. If some of the reactive material undergoes hydrolysis before it has an opportunity to covalently bond with the proteinaceous shell, the resulting hydrolysis product would also form a hydrophobic deposit on the inner surface of the microsphere and act as a sealer.

Alternatively, a polymerizable, low-boiling monomer can be introduced with a water-insoluble gas. Hydrophobic monomers within the present invention polymerize inside the microsphere, optionally as a result of reaction with a chemical initiator or light, to form a polymer layer on the inner surface of the microsphere. The polymeric material formed includes, but is not limited to substituted polyethylene, polystyrene and the like. Preferred polymeric materials include polyacrylate and polymethacrylate.

In the cases described above, a hydrophobic layer is formed which is chemically and/or physically attached to the inner surface of the proteinaceous shell. In another aspect of the invention, the hydrophobic compound forms a sponge-like structure within the proteinaceous shell occupying some or all of the space within the microsphere and contains biocompatible gases within the interstices.

The amount of hydrophobic compound introduced in the shell is an amount sufficient to decrease the permeability of the microsphere shell to the aqueous environment. The decrease in permeability of the shell results in slower rate of gas exchange with the aqueous environment and is evidenced by enhanced pressure resistance of the microsphere. The amount of hydrophobic compound introduced into the microsphere by the carrier gas can be controlled by its partial vapor pressure. Raising or lowering the temperature of a temperature bath containing the hydrophobic compound will increase or decrease, respectively, the size of the hydrophobic layer. For example, air can be saturated with perfluorodecalin (bp. 142° C. at 760 mm Hg) by bubbling the gas through perfluorodecalin that is maintained at 75° C. by standing in a temperature bath. The partial vapor pressure attained will be approximately 100 mm Hg. The saturated gas is then mixed with 1% human serum albumin to form microspheres by a cavitation process.

Microspheres formed by ultrasonication generally have a mean diameter of 3–5 μm and a shell thickness of approximately 20 nm. Saturating the carrier gas with a compound such as perfluorodecalin can increase the shell thickness by 5 to 10% at 100 mm Hg partial vapor pressure. While the specific amount of hydrophobic compound necessary to decrease the permeability of the microsphere will vary with the hydrophobic compound and the gas, the gas generally should be saturated with the hydrophobic compound to give a partial pressure in the range of about 10 to about 650 mm Hg, preferably about 50 to about 250 mm Hg.

Microspheres containing gas saturated with the hydrophobic compound are formed by mechanical or ultrasonic cavitation or by cavitation produced by a colloid mill at an elevated temperature. Upon cooling to room temperature, the hydrophobic compound will condense on the hydrophobic inner membrane surface of the microsphere thereby creating an additional hydrophobic barrier and increasing the overall hydrophobicity of the microsphere shell.

Gases suitable for use within the present invention are pharmacologically acceptable and insoluble and include, but are not limited to, oxygen, nitrogen, noble gas, methane, ethane, propane, butane, pentane, sulfur hexafluoride, perfluoromethane, perfluoroethane, perfluoropropane, perfluorobutane, perfluoropentane and the like.

Suitable microsphere shell material includes proteins and synthetic amino acid polymers. The material is preferably a protein, and more preferably human serum albumin.

The microspheres of the present invention may be made by known methods used to make conventional gas-filled microspheres such as sonication, mechanical cavitation using a milling apparatus, or emulsion techniques.

MODES OF CARRYING OUT THE INVENTION

The present invention relates to a process for increasing the hydrophobicity of microsphere shells by creating a liquid or solid hydrophobic barrier on the inner surface of a microsphere shell. Such a barrier is produced by saturating a gas suitable for use within the present invention with a hydrophobic compound, such as a hydrocarbon or perfluorocarbon or the like, at an elevated temperature. Microspheres are then prepared using conventional cavitation techniques and the hydrophobic compound saturated in the gas will condense and/or react with the shell material and form a liquid or solid hydrophobic barrier on the inner surface of the microsphere shell.

Suitable hydrophobic compounds within the present invention include, but are not limited to, hydrocarbons of the general formula, $C_nH_{2n+2}$, wherein n=6–12, such as octane (bp=26° C.) or isooctane (bp=99° C.), linear or branched perfluorocarbons of the general formula $C_nF_{2n+2}$, wherein n=5–12, such as perfluoropentane (bp=29° C.), perfluorooctane (bp=100° C.) or 1-bromoperfluorooctane (bp=142° C.)

and cyclic perfluorocarbons such as perfluoromethylcyclohexane (bp=76° C.), perfluorodecalin (bp=142° C.), and octafluorotoluene (bp 105° C.). Inert hydrophobic compounds within the present invention include, but are not limited to, perfluorinated alcohols such as 1H,1H-heptafluoro-1-butanol (bp=96° C.), 1H,1H,7H-dodecafluoro-1-heptanol (bp=170° C.), ethers such as 2,3,4,5,6-pentafluoroanisole and esters such as alkyl perfluoroalkanoates.

Reactive hydrophobic compounds include, but are not limited to, active esters such as linear alkyl trifluoracetates or acyl chlorides with the general formula $C_nH_{2+1}COCl$, wherein n=4–10, such as hexanoyl chloride (bp=152° C.) or $C_nF_{2n+1}COCl$, wherein n=2–10, such as perfluorooctanoyl chloride (bp=132° C.) and cyclic compounds such as pentafluorobenzoyl chloride (bp=159° C.). Acid chlorides of some perfluoro alkanedioic acids, such as tetrafluorosuccinyl chloride, hexafluoroglutaryl chloride and octafluoroadipoyl chloride, which are bifunctional and capable of crosslinking proteinaceous material can also serve as hydrophobic compounds. Polymerizable hydrophobic compounds within the present invention include, but are not limited to, styrenes such as pentafluorostyrene (bp=140° C.), alky acrylate, $CH_2=CHCOOR$, wherein $R=C_nH_{2n+1}$ or $C_nF_{2n+1}$, wherein n=1–6 and the corresponding alkyl methacrylates and fluoroalkyl methacrylates.

Suitable shell material must be amphiphilic, i.e., containing both hydrophobic and hydrophilic moieties. It must also be capable of forming a thin layer or skin around the encapsulated gas, which will generally result in hydrophilic groups oriented externally and hydrophobic groups oriented internally. When microspheres are produced to contain insoluble gas, this orientation is believed to be enhanced by the presence of the insoluble gas during microsphere formation.

Protein shells may also optionally incorporate proteins, amino acid polymers, carbohydrates, lipids, sterols or other substances useful for altering the rigidity, elasticity, biodegradability and/or biodistribution characteristics of the shell. The rigidity of the shell can also be enhanced by cross-linking, for example, with irradiation.

Protein shell material includes both naturally-occurring proteins and synthetic amino acid polymers which herein are both generally referred to as being in the class of shell materials described as "proteins". Examples of naturally-occurring proteins include gamma-globulin (human), apotransferrin (human), beta-lactoglobulin, urease, lysozyme, and serum albumin. Synthetic amino acid polymers can optionally be in the form of block or random co-polymers combining both hydrophobic and hydrophilic amino acids in the same or different chains. Moreover, amino acid polymers can optionally be fluorinated.

The present invention also contemplates the attachment of target-specific moieties to the outer shell material of microspheres. Microspheres within the present invention provide a superior delivery vehicle for such target-specific moieties due to the increased stability of the microspheres. Such increased in vivo stability insures delivery of target-specific moieties to targeted organs or cells via lengthy routes of administration.

The introduction of the hydrophobic compound in the shell is accomplished by forming microspheres at elevated temperatures in the presence of a gas saturated with a hydrophobic compound having a boiling point above 20° C. For example, air or perfluoropropane can be saturated with perfluorooctane or perfluorodecalin having a boiling point of 99° C. and 141° C., respectively. The saturated gas is maintained at a temperature above the bath temperature and mixed with 1–5% human serum albumin to form microspheres by a cavitation technique.

Microspheres containing the hydrocarbon barrier may be made by known methods used to make conventional gas-filled microspheres such as sonication, mechanical cavitation using a milling apparatus, or emulsion techniques. Such techniques are exemplified in U.S. Pat. Nos. 4,957,656; 5,137,928; 5,190,982; 5,149,543: PCT Application Nos. WO 92/17212; WO 92/18164; WO 91/09629; WO 89/06978; WO 92/17213; GB 91/00247; and WO 93/02712: and EPA Nos. 458,745 and 534,213 which are incorporated herein by reference.

Gases suitable for use within the present invention are pharmacologically acceptable, i.e., biocompatible and minimally toxic to humans. The term "biocompatible" means the ability of the gas to be exhaled or metabolized without the formation of toxic by-products. The term "gas" refers to any compound which is a gas or capable of forming gas at the temperature at which imaging is being performed (typically normal physiological temperature) or upon application of ultrasound energy. The gas may be composed of a single compound or a mixture of compounds. Examples of gases suitable for use within the present invention are air, $O_2$, $N_2$, $H_2$, $CO_2$, $N_2O$; noble gases such as argon, helium, xenon; hydrocarbon gases such as methane, ethane, propane, n-butane, isobutane and pentane, and perfluorocarbon gases such as perfluoromethane, perfluoroethane, perfluoropropane, perfluorobutane, perfluoroisobutane and perfluoropentane. The gas is preferably a perfluorocarbon which is insoluble in water, which intends a solubility of less than 0.01 Ml of gas per Ml of water at atmospheric pressure and a temperature of 25° C. This degree of insolubility results in maximum stability in vitro and persistence in vivo. Solubility can be determined by any appropriate method. See, for example, Wen-Yang Wen et al. (1979) *J. Solubility Chem.* 8(3):225–246.

Microspheres made by processes within the present invention are echogenic (i.e., capable of reflecting sound waves) being composed of material having acoustic properties which are significantly different from those of blood or tissue. The maximum size (mean diameter) of the microsphere is defined by that size which will pass through the pulmonary capillaries. In the case of humans, that size will typically be less than about 10 micrometers. Correspondingly, the minimum size is that which will provide efficient acoustic scattering at the ultrasonic frequencies typically used for ultrasonic imaging. (The frequency may vary with the mode of imaging, e.g., transthoracic, transesophageal, and will normally be in the range of 2–12 MHz.) The minimum size will typically be about 0.1 micrometers. The typical mean size of the microspheres used in the invention method will be about 2 to about 7 micrometers. This size will permit their passage through capillaries, if necessary, without being filtered out prior to reaching the area to be imaged (e.g., where a peripheral venous injection site is used). Thus, microspheres within the present invention will be capable of perfusing tissue and producing an enhanced image of the tissue, organs and any differentiation between well-perfused and poorly-perfused tissue, without being injected into the arteries or directly into the area to be imaged. Accordingly, they may be injected into a peripheral vein or other predetermined area of the body, resulting in considerably less invasion than the arterial injections required for an angiogram.

Microspheres made by processes within the present invention may be used for imaging a wide variety of areas.

These areas include, but are not limited to, myocardial tissue, liver, spleen, kidney, and other tissues and organs presently imaged by ultrasonic techniques. Use of microspheres within the present invention may result in an enhancement of such currently obtainable images.

In terms of method of operation, the use of the subject microspheres would be the same as that of conventional ultrasonic contrast agents. The amount of microspheres used would be dependent on a number of factors including the choice of liquid carriers (water, sugar solution, etc.), degree of opacity desired, areas of the body to be imaged, site of injection and number of injections. In all instances, however, sufficient microspheres would be used in the liquid carrier to achieve enhancement of discernable images by the use of ultrasonic scanning.

The invention is further illustrated by the following examples. These examples are not intended to limit the invention in any manner.

EXAMPLE 1

Preparation of Gas-filled Microsphere Containing a Liquid Hydrophobic Barrier by Mechanical Cavitation (A) Saturation of Gas The carrier gas is saturated with the hydrophobic compound by bubbling it via a fritted gas dispersion tube through the hydrophobic compound which is maintained in a constant temperature bath. The temperature is adjusted to maintain the required partial vapor pressure. The temperature of the gas line leading to the cavitation chamber must be maintained at or above the bath temperature in order to prevent condensation of the hydrophobic compound from the gas-vapor mixture before it reaches the chamber.

(B) Preparation of Microspheres

A 5% human albumin solution (USP) is deaerated under continuous vacuum for two hours. The vacuum is released by filling the evacuated vessel with the carrier gas described in ¶ A above. The solution is adjusted to a temperature (about 68° C.) necessary to achieve local denaturation of the albumin upon cavitation via an in line heat exchanger and pumped at about 100 mL/min into a colloid mill, for example, a 2" colloid mill (Greerco, Hudson N.H. model W250V or AF Gaulin, Everett, Mass., model 2F). The gas-vapor mixture is added to the liquid feed just upstream of the inlet port at a flow rate of about 120–220 mL/min. The gap between the rotor and the stator is adjusted to about 3/1000th inch and the albumin solution is milled continuously at about 7000 rpm at a process temperature of about 73° C.

The dense white solution of microspheres thus formed is immediately chilled to a temperature of about 10° C. by a heat exchanger, and collected in glass vials. The vials are immediately sealed.

EXAMPLE 2

Method of Making Microspheres by Sonic Cavitation

Air, at a flow rate of 15 ml/minute, was saturated with perfluoropentane at 28° C. as described in Example 1 above prior to undergoing continuous sonication with 1% human serum albumin (flow rate of 80 ml/minute) as described by Cerny (U.S. Pat. No. 4,957,656). The dense white solution of microspheres thus formed was immediately chilled to a temperature of about 10° C. by a heat exchanger and collected in glass vials. The vials are immediately sealed.

Upon standing, the microspheres were floating in a white top layer. The average particle size was 3–5 μm diameter with a concentration of $2 \times 10^9$/ml.

In a second experiment, 100 ml of 1% human serum albumin and 8 ml of liquid perfluoropentane were sonicated (900 watts, 20 KHz) under 85 psi air pressure until the temperature reached 73.4° C. After the power was turned off, the temperature increased slightly to 74.6° C. The resulting mixture was left in a separation funnel for 1 day at 4° C. A layer of heavy microspheres settled to the bottom and was separated from a foamy top layer. The concentration of the microspheres was $3.2 \times 10^9$/ml with an average particle size of 1.9 μm.

EXAMPLE 3

Additional Preparation of Gas-filled Microsphere Containing a Liquid Hydrophobic Barrier by Mechanical Cavitation Perfluoropropane at a flow rate of 42 mL/minute was saturated with perfluorohexane at 34° C. as described in Example 1 prior to undergoing continuous sonication with 1% human serum albumin (flow rate of 80 mL/minute) as described by Cerney (U.S. Pat. No. 4,957,656). The dense white solution of microspheres thus formed was quickly chilled to a temperature of about 10° C. by a heat exchanger and collected in glass vials. The vials are immediately sealed. Upon standing, the microspheres were floating in a white top layer. The average particle size was 3.6 μm with a concentration of $8.5 \times 10^8$.

EXAMPLE 4

Diagnostic Imaging

Microspheres prepared as described in Examples 1, 2 and 3 above are used in diagnostic imaging as follows: For a dog weighing approximately 25 kg, a 1.0 mL volume of a microsphere suspension containing $5 \times 10^7$ to $5 \times 10^9$ microspheres per mL is injected into a peripheral (cephalic) vein at a rate of 0.3 mL per second. Images of the heart are acquired using a Hewlett Packard Sonos 1500 (Andover, Mass.) ultrasonograph in the B-mode using a transthoracic 5.0 mHz transducer. Images are recorded at a frame rate of 30 frames per second throughout the procedure and stored on S-VHS tape for later processing.

What is claimed is:

1. A process for making gas-filled, pressure resistant microspheres containing a hydrophobic barrier within said microsphere shell, comprising:

(a) saturating a gas with a hydrophobic compound having a boiling point above room temperature;

(b) mixing said saturated gas with a solution of a microsphere shell material at a temperature above room temperature;

(c) forming microspheres by cavitation; and (d) forming a liquid or solid hydrophobic barrier on the inner surface of the microsphere shell by cooling said microspheres to a temperature which is sufficient to substantially condense the hydrophobic compound, said temperature being below room temperature.

2. The process of claim 1 wherein the hydrophobic compound is a linear or branced hydrocarbon of the general formula $C_nH_{2n+2}$, wherein n=6–12, or a linear or branched perfluorocarbon of the general formula $C_nF_{2n+2}$ wherein n=5–12, or a cyclic perfluorocarbon, or a perfluorinated alcohol or ether, or a alkyl trifluoroacetate or acyl chloride of the general formula $C_nH_{2n+1}COCl$ wherein n=4–10, or a perfluorinated acyl chloride of the general formula $C_nF_{2n+1}COCl$ wherein n=4–10, or a polymerizable styrene or alkyl acrylate of the general formula $CH_2$=CHCOOR, wherein R=$C_nH_{2n+1}$, or $C_nF_{2n+1}$, wherein n=1–6, and corresponding alkyl methacrylates and fluoroalkyl methacrylates.

3. The process of claim 1 wherein the hydrophobic compound is perfluoropentane.

4. The process of claim 1 wherein the hydrophobic compound is an alkyl acrylate.

5. The process of claim 1 wherein the hydrophobic compound is an alkyl methacrylate.

6. The process of claim 1 wherein the gas is insoluble.

7. The process of claim 6 wherein the gas is a perfluorocarbon gas.

8. The process of claim 1 wherein said barrier is a layer that covalently bonds to the inner surface of said microsphere shell.

9. The process of claim 1 wherein said barrier is an inert layer that condenses on the inner surface of said microsphere shell.

10. The process of claim 1 wherein said barrier is a polymerized layer that forms on the inner surface of said microsphere shell.

11. The process of claim 1 wherein said barrier is a sponge-like structure that forms within said microsphere shell.

12. The process of claim 1 wherein cavitation is achieved mechanically.

13. The process of claim 1 wherein cavitation is achieved by sonication.

14. The process of claim 1 wherein cavitation is achieved by use of a colloid mill.

15. The process of claim 1 further comprising covalently bonding at least one target-specific moiety to said microsphere shell.

* * * * *